United States Patent [19]

Yule

[11] Patent Number: 4,898,168

[45] Date of Patent: Feb. 6, 1990

[54] INFLATION INDICATORS FOR CUFFED TUBES

[75] Inventor: Bruce Yule, Hythe, England

[73] Assignee: Smiths Industries Public Limited Company, London, England

[21] Appl. No.: 294,772

[22] Filed: Jan. 9, 1989

[30] Foreign Application Priority Data

Jan. 9, 1988 [GB] United Kingdom ................. 8800447

[51] Int. Cl.$^4$ ........................................... A61M 25/00
[52] U.S. Cl. .................................. 128/207.15; 604/99
[58] Field of Search ................................. 604/96–100; 128/207.15, 344; 116/DIG. 8

[56] References Cited

U.S. PATENT DOCUMENTS 4,178,939 12/1979 Stephens ................................. 604/99
4,407,281 10/1983 Brandt et al. ......................... 604/100

Primary Examiner—Stephen C. Pellegrino
Attorney, Agent, or Firm—Pollock, Vande Sande & Priddy

[57] ABSTRACT

An inflation indicator for a cuffed tracheal tube has a plastics envelope with two walls sealed around their edges. An elongate indentation is formed along the inner surface of each wall along the length of the envelope to provide a continuous fluid passage between the walls, between a valved coupling and an inflation lumen, when the walls contact one another on collapse of the envelope.

9 Claims, 1 Drawing Sheet

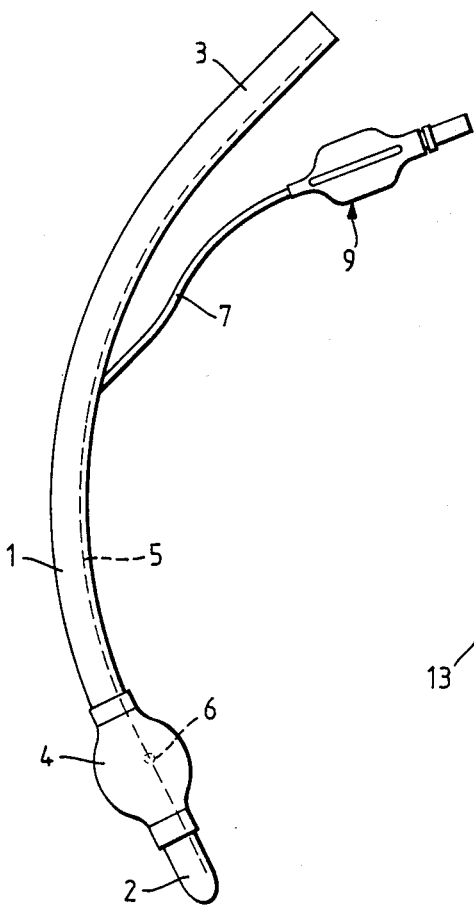
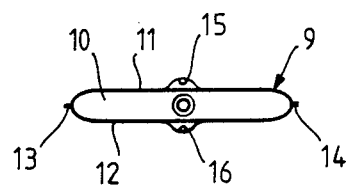
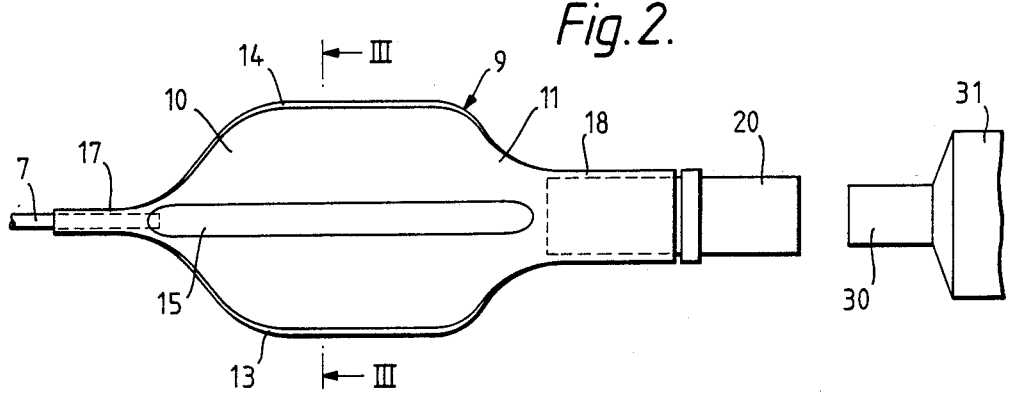

INFLATION INDICATORS FOR CUFFED TUBES

BACKGROUND OF THE INVENTION

This invention relates to inflation indicators for cuffed tubes.

Medico-surgical tubes that are required to be inserted and sealed in a body passage or cavity are commonly provided with an inflatable cuff encircling the tube. The cuff is inflated via an inflation lumen to seal the tube with the body passage or cavity. In order to provide an indication of whether or not the cuff is inflated, the inflation line can support an inflation indicator in the form of a flexible envelope the interior of which communicates with the inflation line and hence with the interior of the cuff. Inflation of the cuff causes a corresponding inflation of the envelope which is readily apparent to the clinician.

The cuff on the tube is usually inflated by means of an air-filled syringe the nose of which is coupled to a coupling on the machine end of the inflation line. When it is necessary to remove the tube, the cuff is deflated in a similar way by means of a syringe, the plunger of which is withdrawn to suck air from the cuff.

One problem with this, is that the fall in pressure caused by withdrawing the plunger can cause the wall of the envelope to collapse together and seal off the gas passage to the cuff. This can be a particular disadvantage in an emergency where it may be necessary to remove the tube quickly. There is also a tendency for the inflation indicating envelope to seal off if it is bent or folded across the gas passage through it.

BRIEF SUMMARY OF THE INVENTION

It is an object of the present invention to provide an inflation indicator that can be used to alleviate this problem.

According to one aspect of the present invention there is provided an inflation indicator for a cuffed medico-surgical tube formed from an envelope with two opposite walls of a flexible gas-impermeable material, the envelope having respective fluid inlets at opposite ends of which communicates with the cuff on the medico-surgical tube such that the envelope is inflated by pressure in the cuff, at least one of the walls having a surface formation extending along the length of the envelope on the inner surface of the wall to provide a continuous fluid passage between the walls between the two inlets when the walls contact one another on collapse of the envelope.

The surface formation is preferably formed integrally with the wall and may be an elongate indentation on the inner surface of the wall. The surface formation is preferably provided on both the walls. The envelope may be a plastics sleeve that is subsequently flattened. The indicator may include a valved coupling sealed in one end of the envelope.

According to another aspect of the present invention there is provided a cuffed medico-surgical tube including an inflation indicator according to the above one aspect of the present invention.

A cuffed endotracheal tube assembly including an inflation indicator according to the present invention, will now be described, by way of example, with reference to the accompanying drawings.

BRIEF DESCRIPTION OF THE DRAWINGS

FIG. 1 is a plan view of the tube assembly;
FIG. 2 is a plan view of the inflation indicator to a larger scale; and
FIG. 3 is a transverse section of the inflation indicator along the line III—III of FIG. 2.

DETAILED DESCRIPTION

With reference to FIG. 1, there is shown a cuffed endotracheal tube assembly comprising a curved plastics tube 1 that is open at both ends. The patient end 2 of the tube is adapted for insertion into the trachea of a patient, with the machine end 3 projecting from the patient's mouth. Close to the patient end 2 of the tube 1, a flexible cuff 4 encircles the tube for use in sealing the tube with the interior of the patient's trachea.

An inflation lumen 5 extends along the tube 1 within its wall and is closed at the patient end 2 and machine end 3 of the tube. The lumen 5 opens into the interior of the cuff 4 through an opening 6 in the outer surface of the tube wall. A small-bore inflation line 7 is coupled at one end with the lumen 5 through an opening in the tube wall. The other end of the inflation line 7 is coupled to an inflation indicator 9 as shown in greater detail in FIGS. 2 and 3.

The inflation indicator 9 includes a flexible envelope 10 of a gas-impermeable material such as PVC. The envelope 10 may be made from an extruded or blow-moulded sleeve of PVC that is subsequently flattened to provided two substantially flat opposite walls 11 and 12 joined at their lateral edges 13 and 14. Each wall 11 and 12 has an integral elongate surface formation in the form of a groove or indentation 15 and 16 respectively on the inner surface that extends centrally of each wall along its length. The patient end 17 of the envelope 10 is joined and sealed to the outer surface of the machine end of the inflation line 7, so that the inflation line opens into the envelope. The opposite, machine end 18 of the envelope 10 is sealed about one end of a valved coupling 20 of conventional form. The other end of the coupling is adapted to receive the nose 30 of a syringe 31 used to inflate and deflate the cuff 4.

In use, the patient end of the tube 1 is inserted in the patient's trachea with the cuff 4 in a deflated condition. The nose 30 of the syringe 31 is then inserted in the coupling 20 and the plunger of the syringe is depressed so as to force a measured quantity of air into the cuff 4 via the inflation indicator 9, inflation line 7 and inflation lumen 5. This also causes the inflation indicator 9 to be inflated, with the walls 11 and 12 separated and of more rounded surface. The syringe 31 can then be withdrawn and the coupling capped if desired.

When it is necessary to remove the tube from the trachea, the syringe 31 is reinserted in the coupling 20 and the plunger is withdrawn so as to apply negative pressure and suck air out of the cuff 4. If this should happen too quickly, the walls 11 and 12 of the envelope 10 can be sucked together. In the present indicator 9, however, there is little risk of this interrupting withdrawl of air from the cuff 4 because the grooves 15 and 16 ensure that there is always a gas passage between the opposite ends of the inflation indicator. The grooves 15 and 16 also help ensure a gas passage between opposite ends of the indicator if the indicator envelope 10 is slightly bent.

It will be appreciated that various different surface formations on the inside of the envelope could be used to ensure a gas passage along it. The surface formation could, for example, be provided by separately made ribs subsequently affixed to the inside surface of the walls.

The indicator can be used with other cuffed medico-surgical tubes, not just tracheal tubes.

What is claimed is:

1. An inflation indicator of the kind for a cuffed medico-surgical tube formed from an envelope with two opposite walls of a flexible gas-impermeable material, the envelope having respective fluid inlets at opposite ends one of which communicates with the cuff on the medico-surgical tube such that the envelope is inflated by pressure in the cuff, the improvement wherein one of said walls has a surface formation extending along the length of the envelope on an inner surface of the wall to provide a continuous fluid passage between the walls between the two inlets when said walls contact one another on collapse of the envelope.

2. An inflation indicator according to claim 1, wherein said surface formation is formed integrally with the wall.

3. An inflation indicator according to claim 1, wherein said surface formation is an elongate indentation on the inner surface of the wall.

4. An inflation indicator according to claim 1, wherein said surface formation is provided on both of said walls.

5. An inflation indicator according to claim 1, wherein the envelope is a plastics sleeve and wherein the sleeve is flattened.

6. An inflation indicator according to claim 1, wherein the indicator includes a valved coupling, and wherein said valved coupling is sealed in one end of the envelope.

7. An inflation indicator for a cuffed medico-surgical tube, said indicator comprising: an envelope, said envelope having respective fluid inlets at opposite ends, means connecting one of the said fluid inlets with a cuff on said tube such that said envelope is inflated by pressure in the cuff, said envelope having two opposite walls of a flexible gas-impermeable material, each said wall having a respective elongate indentation entending along the length of the envelope on an inner surface of the wall such that when the walls contact one another on collapse of the envelope a continuous fluid passage is provided between the two inlets along said elongate indentations.

8. A cuffed tracheal tube assembly comprising: a tracheal tube having a cuff thereon, and a inflation indicator, said indicator comprising an envelope, said envelope having respective fluid inlets at opposite ends, means connecting one of the said fluid inlets with said cuff such that said envelope is inflated by pressure in the cuff, said envelope having two opposite walls of a flexible gas-impermeable material, at least one of said walls having a surface formation extending along the length of the envelope on an inner surface of the wall to provide a continuous fluid passage between the walls between the two inlets when said walls contact one another on collapse of the envelope.

9. A cuffed tracheal tube assembly comprising a tracheal tube having a cuff thereon and an inflation indicator, said indicator comprising an envelope, said envelope having respective fluid inlets at opposite ends, means connecting one of the said fluid inlets with said cuff such that said envelope is inflated by pressure in the cuff, said envelope having two opposite walls of a flexible gas-impermeable material, each said wall having a respective elongate indentation on an inner surface of the wall such that when the walls contact one another on collapse of the envelope a continuous fluid passage is provided between the two inlets along said elongate indentations.

* * * * *